United States Patent [19]

Strain et al.

[11] 4,272,247

[45] Jun. 9, 1981

[54] CONTINUOUS-FLOW FREE ACID MONITORING METHOD AND SYSTEM

[75] Inventors: James E. Strain, Kingston; Harley H. Ross, Oak Ridge, both of Tenn.

[73] Assignee: The United States of America as represented by the United States Department of Energy, Washington, D.C.

[21] Appl. No.: 111,496

[22] Filed: Jan. 11, 1980

[51] Int. Cl.³ .................... G01N 27/10; G01N 27/06
[52] U.S. Cl. .............................. 23/230 R; 23/232 R; 23/232 E; 23/230 A; 422/90; 422/62; 422/81
[58] Field of Search ............. 23/230 R, 232 E, 232 R, 23/230 A; 422/62, 81, 90; 73/23, 27 R

[56] References Cited

U.S. PATENT DOCUMENTS

| | | | |
|---|---|---|---|
| 2,949,345 | 8/1960 | Clauss | 23/232 E |
| 3,367,747 | 2/1968 | Sieth et al. | 23/232 R |
| 3,904,365 | 9/1975 | Larson et al. | 23/230 R |
| 3,915,646 | 10/1975 | Harris et al. | 23/232 E |

*Primary Examiner*—Ronald Serwin
*Attorney, Agent, or Firm*—David E. Breeden; Stephen D. Hamel; Richard G. Besha

[57] ABSTRACT

A free acid monitoring method and apparatus is provided for continuously measuring the excess acid present in a process stream. The disclosed monitoring system and method is based on the relationship of the partial pressure ratio of water and acid in equilibrium with an acid solution at constant temperature. A portion of the process stream is pumped into and flows through the monitor under the influence of gravity and back to the process stream. A continuous flowing sample is vaporized at a constant temperature and the vapor is subsequently condensed. Conductivity measurements of the condensate produces a nonlinear response function from which the free acid molarity of the sample process stream is determined.

10 Claims, 7 Drawing Figures

CONTINUOUS-FLOW FREE ACID MONITORING METHOD AND SYSTEM

The invention is a result of a contract with the U.S. Department of Energy.

BACKGROUND OF THE INVENTION

The present invention relates generally to free acid measuring devices and methods and more specifically, it relates to a continuous-flow, monitoring system and method for the measurement of the free acid concentration in a process stream.

Aqueous reprocessing of spent nuclear reactor fuel involves the initial dissolution of fragmented fuel bundles in strong acid, usually nitric acid. This solution is then clarified by filtration or centrifugation and made up to a desired acidity prior to extraction of the uranium and plutonium. During the dissolution stage, the acid concentration becomes unpredictably altered. The free acid concentration is crucial at this point, must be measured and adjusted to the proper acidity prior to extraction of uranium and plutonium. Excessively high acid concentration results in incomplete separation of fission products from the uranium and plutonium, and concentrations below the desired level result is losses of uranium and plutonium. The nature of the solution with respect to radioactivity and inhomogeneity make sampling and free acid determination by conventional methods difficult and time consuming. It has generally been the practice to randomly sample the process stream and make acid determinations by direct titration. This requires considerable hold-up time and prevents the immediate return of the sample to the process stream. Further, handling of the samples must be done in a hot cell due to the high radiation levels present in the early stages of fuel reprocessing streams. Thus, there is a need for a method and a system for an accurate determination of free acid that is compatible with a continuous operation in a hostile environment.

Therefore, it is an object of this invention to provide a continuous-flow method for measuring the free acid in a process stream.

Another object of this invention is to provide a system for in-line monitoring of free acid in the process stream.

Other objects, advantages and novel features of the invention will become apparent to those skilled in the art upon examination of the following detailed description of the invention taken in conjunction with the accompanying drawings.

SUMMARY OF THE INVENTION

A method and apparatus are provided for the continuous monitoring of the free acid concentration in a process stream. A continuous sample is pumped into the monitoring system so that it flows through the system by the influence of gravity and returned to the process stream. A saturated vapor of the flowing stream is generated in a constant temperature evaporator. The vapor phase is then transported at an elevated temperature by means of a low-velocity gas stream passing through the evaporator to a condenser where the vapor is condensed. The condensate is collected and the partial pressure ratio of water and acid of the condensate is determined. The free acid of the original flowing sample solution is determined from the partial pressure ratio measurement.

The system for carrying out the method of monitoring the free acid process stream may be remotely controlled so that the system may be operated in a hostile environment. In process streams to be monitored which may contain dissolved oxides of nitrogen an airlift may be used to elevate the sample for flow through the system. The airlift acts to aerate the sample to remove dissolved oxides of nitrogen through sparging of the sample by the lift airstream. The air and liquid phases are then separated before the liquid phase enters the constant-temperature evaporator.

DETAILED DESCRIPTION

Figure 1:
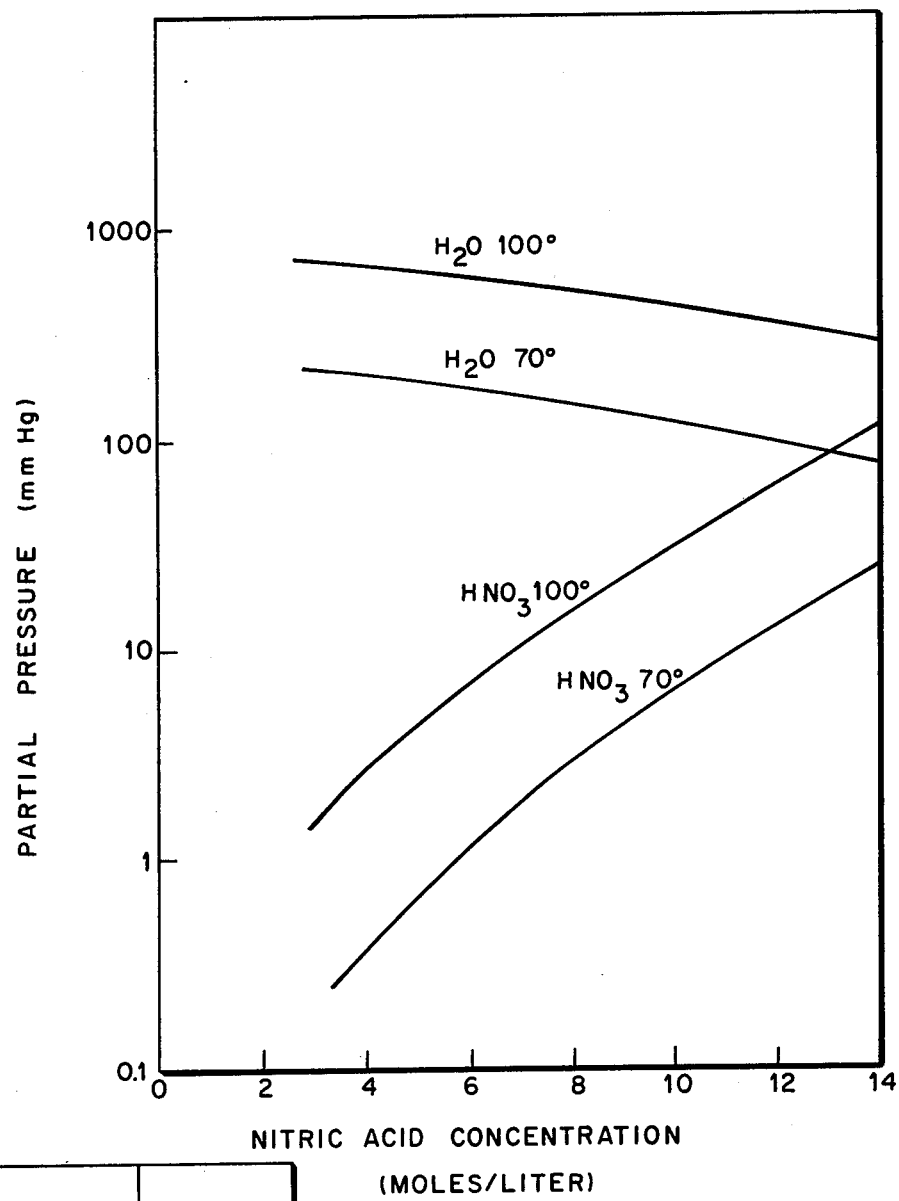
FIG. 1 is a graph illustrating the partial pressures of $H_2O$ and $HNO_3$ as a function of nitric acid concentration at constant temperature.

Turning now to the drawings, first to FIG. 1, the invention will be described, both the method and the apparatus, as embodied in a system for continuously monitoring the free nitric acid in a nuclear fuel reprocessing stream. It will be obvious to those skilled in the art that the system may be used for monitoring other acids in different systems and is not limited to the measurement of free nitric acid in a nuclear fuel reprocessing stream. The method is based upon the ratio of partial pressures of water and acid of the sample at constant temperature as a function of acid concentration. FIG. 1 shows the partial pressure of water and $HNO_3$ at 70° C. and 100° C. The data used to construct the curves of FIG. 1 are taken from the open literature such as "Gmelins Handbuch Der Anorgan Chemie" 8 Auflage, N p. 977–980. It will be seen from the graph that if the ratio of the partial pressures of water ($pH_2O$) and $HNO_3$ ($pHNO_3$) is measured above an acid solution held at a constant temperature, the ratio $pH_2O/pHNO_3$ may be related to the acidity of the original solution. The ratio may be determined directly by measurement of the acidity of the condensate formed by condensing the equilibrium vapor phase that exists above an acid solution whose temperature is held constant. Measurement of the acidity of the condensate may be accomplished either by direct titration, conductivity, or refractive index measurement. The illustrated apparatus and method employs the conductivity measurement method and is preferred due to its simplicity and continuous response.

Figure 2:
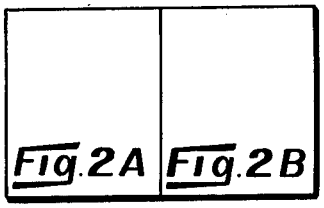
FIG. 2, which consists of FIGS. 2A and 2B arranged as shown in FIG. 2, is a schematic drawing of a free acid monitor in accordance with the present invention.
Figure 2A:
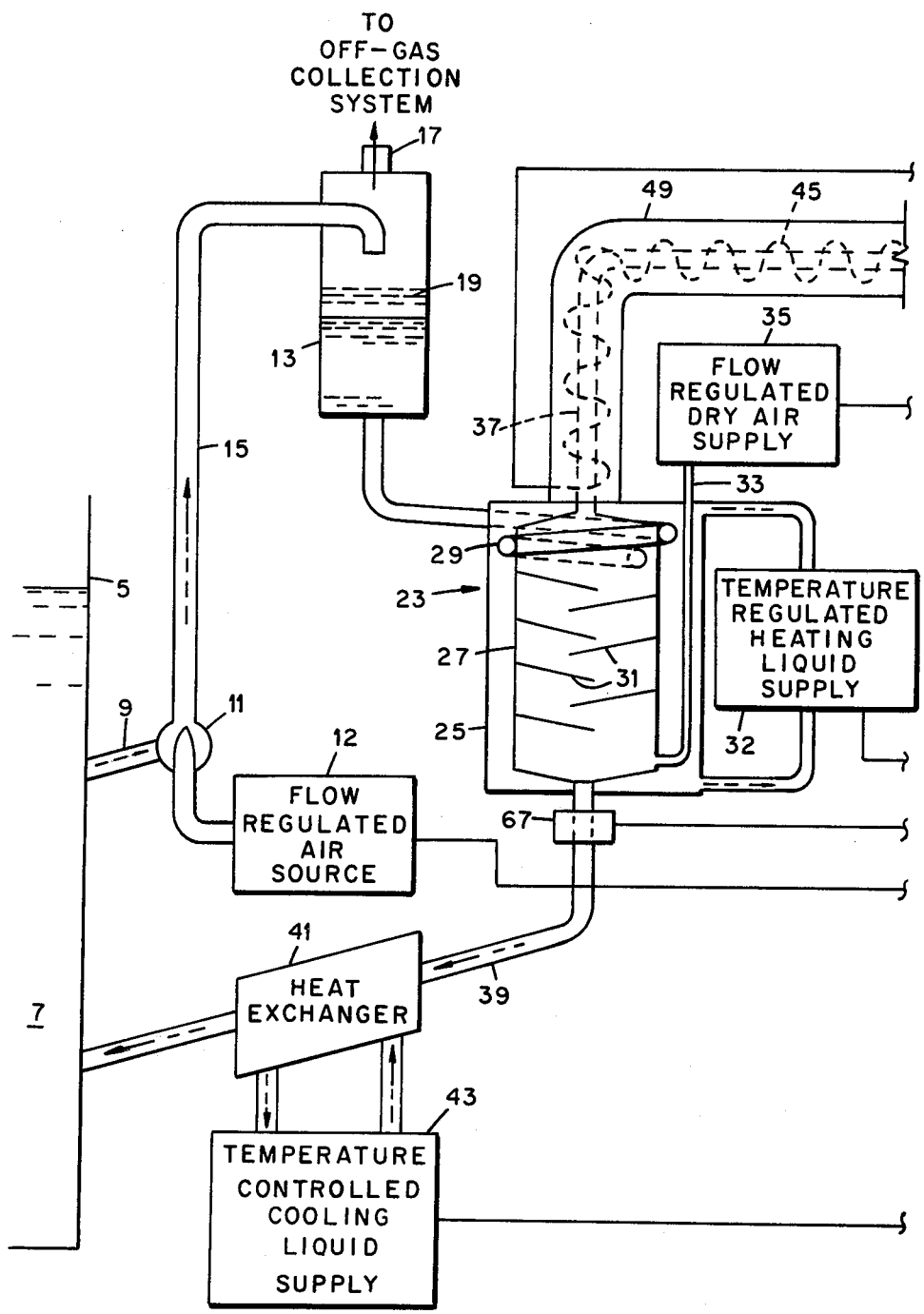
Figure 2B:
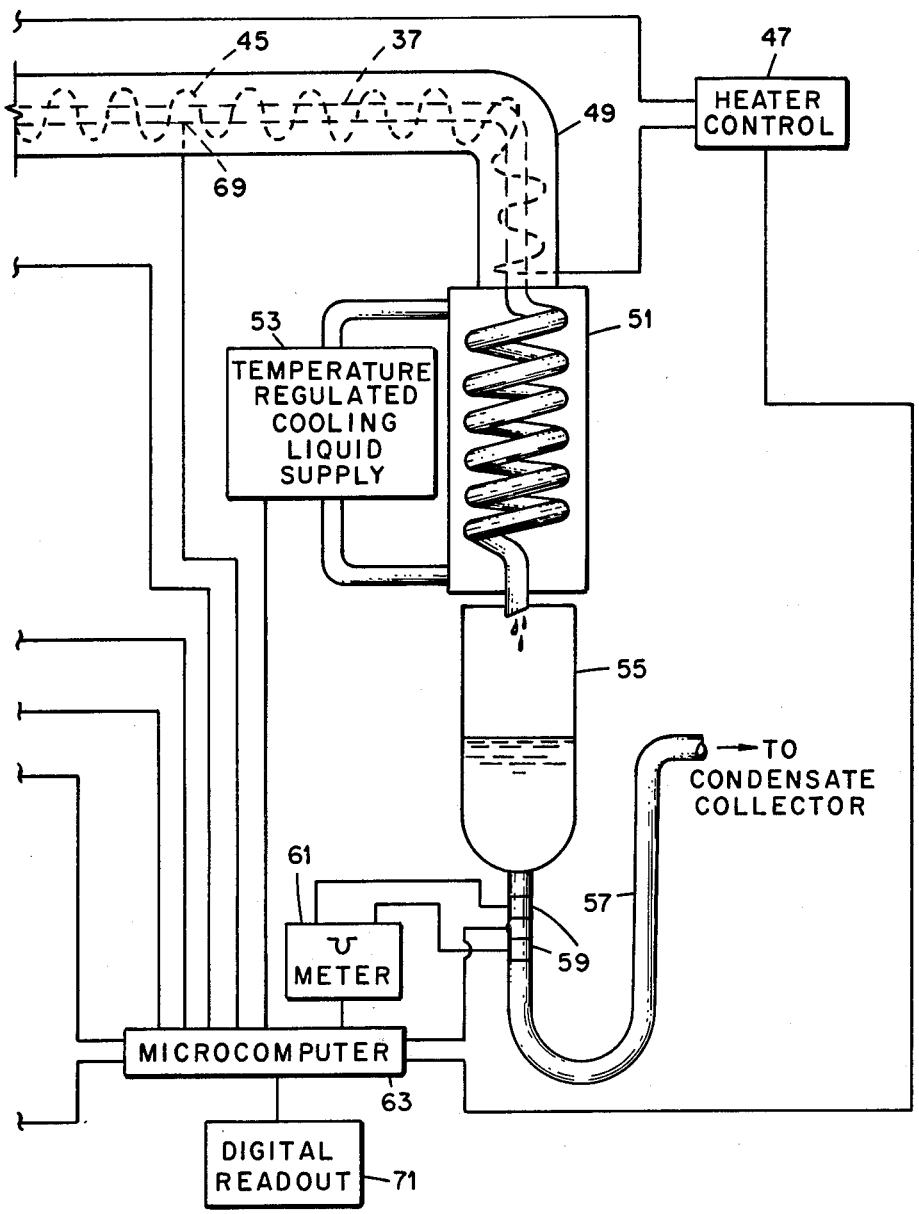

Referring now to FIG. 2 which consists of FIGS. 2A and 2B aligned as shown in FIG. 2, an embodiment of a remote-controlled free acid monitoring system made in accordance with the present invention will be described in which the method of the present invention may be practiced. In this illustration a hold-up vessel 5 in the process stream of a nuclear fuel reprocessing system is provided in which the fuel element particles to be reprocessed are dissolved in a nitric acid solution 7 filling the vessel 5. Samples of the acid solution 7 are drawn from the vessel 5 through an outlet pipe 9 and lifted by means of an airlift pump 11 into a separation vessel 13 through the airlift exit tube 15. The air and liquid phases of the sample are separated in the vessel 13 with the air being vented to an off gas collection system through an exit vent pipe 17. The separator 13 is provided with a stacked coarse screen or baffle arrangement 19 which provides a small pressure differential to aid in separating the gas from the liquid sample. The sample leaves the separator 13 through an exit tube 21 in the bottom of the chamber 13 and flows by gravity to an evaporator 23. The evaporator 23 includes an outer casing 25 through which temperature regulated heating liquid flows from a supply 32 to maintain a constant temperature vaporization of a portion of the sample within an evaporator vessel 27. The sample entering the evaporator 23 through the pipe 21 is first preheated by passing through a heat exchange coil 29 prior to entering the top of the evaporator vessel 27. The sample liquid cascades over interleaved baffles 31 positioned within the evaporator vessel 27. The baffles 31 are partially interleaved to provide greater air-to-liquid contact and minimize aerosol formation. Dry air is introduced at the bottom of evaporator vessel 27 through an inlet pipe 33 from a flow-regulated dry air supply 35 to carry the acid vapor generated in the vessel into a transport tube 37.

The liquid sample which is not evaporated leaves the evaporator vessel 27 through a drain pipe 39 in the bottom of the vessel which passes through a heat exchanger 41 and returns the remaining sample to the vessel 5. The heat exchanger 41 cools the liquid passing back into the process stream to its original temperature by means of cooling liquid from a temperature control cooling liquid supply 43.

The vapor entering the transport tube 37 is heated to maintain the vapor at a temperature above 125° C. This is accomplished by an electric resistance heating strip 45 wrapped about the transport tube 37. The heating strip 45 is connected to a heater-control circuit 47. Further, the transport tube is insulated by means of insulating material 49 disposed about the tube 37. By keeping the temperature of the transport tube above 125° C., the acid vapor remains in the vapor phase and is prevented from condensing on the walls of the tube 37 as it is transported to a condenser 51. The temperature of the condenser 51 is controlled by a temperature-regulated cooling-liquid supply 53 which passes cooling liquid through the condenser 51.

The acid vapor after being converted to a liquid in the condenser 51 enters the enlarged portion of a conductivity cell 55 and flows through an exit line 57 to an appropriate condensate collector or back to the process stream. The exit flow tube is provided with a pair of platinum electrodes 59 which are connected to a conductivity-measuring meter 61. The conductivity cell remains full by virtue of the overflow level of exit tube 57.

Since the system is to be operated remotely, a microcomputer 63 is provided and properly programmed to maintain the various temperatures and flow rates within the system and record the conductivity measurements through the conductivity meter 61 automatically. In order to accomplish the automatic control, the microcomputer 63 constantly measures and controls the flow rates and the various temperatures to the system as will now be described.

Initally the flow is established by regulating the flow of the air from air source 12 into the lift pump 11. As pointed out above, the necessity of the airlift-type pump in this embodiment is to aid in sparging the sample with air to remove dissolved oxides of nitrogen, such as $NO_2$. It was found that $NO_2$ causes erroneously high readings of acidity by virtue of its vaporization in the evaporator chamber 27 and redissolved in the condensate from which the sample acidity is measured. In this particular embodiment an air flow rate of 12 liters per minute was found to reduce the concentration of $NO_2$ entering the evaporator chamber 27 to an acceptable level. In the system shown, a lift of 30 centimeters was found sufficient. With the air flow rate regulated at 12 liters per minute, the sample flow rate is 500 milliliters per hour which gives adequate sample flow and is least affected by changes in lift height or sample density. Further, this flow rate is high enough to transit the evaporator chamber 27 without a measurable change in acidity due to a loss of water or acid to the vapor phase. It will be obvious that in systems in which small volumes of sample are present there will be a slow change in acidity of the sample with time unless the condensate is returned to the process stream.

The flow rate of the sample through the evaporator vessel 27 may be verified by monitoring the temperature of the excess sample exiting vessel 27 through line 39. This is accomplished by using a temperature transducer 67 located to measure the temperature of the excess sample leaving the evaporator. The output of the transducer 67 is connected to an input of the microcomputer 63. The temperature of the evaporator is maintained at a selected constant temperature (73° C. in this embodiment) by the temperature regulated heating liquid supply 32 which is controlled by the microcomputer 63.

Figure 3:
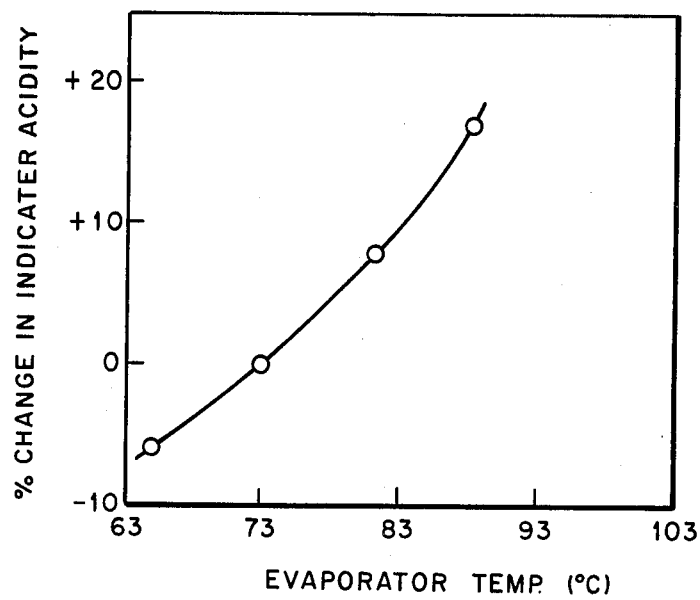
FIG. 3 is a graph which shows the effect of evaporator temperatures on the free acid monitor's response.

The response of the monitor to changing evaporator temperature is shown in FIG. 3. Since the partial pressures of water and nitric acid are not equally effected by a change in temperature, the condensate acidity of the given feed acid sample will increase with increasing evaporator temperature. From the curve of FIG. 3 it will be seen that a 5° C. change in evaporator temperature from 73° C. will produce a change in the indicated acidity of approximately 5%. At higher evaporator temperatures there is larger error for the same variation in temperature. Thus, it will be appreciated that the evaporator vessel 27 temperature must be maintained constant at the selected temperature which may be accomplished by properly insulating the jacket 25 and closely controlling the heating liquid flow and temperature.

Dry air from the source 35 and supply tube 33 is swept through the evaporator vessel 27 at a rate of 0.5 liters per minute under control of the computer 63. The air is used to carry the acid vapor into the transport tube 37 through which it is transported to the condenser 51. The temperature of the transfer tube 37 has been found to have a profound effect on the condensate conductivity. If the wall temperature of the transfer tube falls below 122° C., the boiling point of 15.7 molar nitric acid, the $HNO_3$ vapor condenses to form points of secondary evaporation. These droplets, in addition to reducing the concentration of $HNO_3$ in the vapor phase, are swept into the condenser at random intervals to produce serious fluctuations of the measured conductivity of the condensate. Thus, the temperature of the transport tube 37 is controlled by controlling the current through the heating strip 45 through heater control 47 operated by the computer 63. A thermister 69 is connected to the transport tube 37 to monitor the temperature of the transport tube wall. Its analog signal output is connected to an input of the computer 63 for feedback to aid in control of the transfer tube 37 temperature which is maintained at a temperature of at least 125° C. Temperature variation above 125° C. has no effect on the monitor's response and the transfer tube may be of any convenient length. This makes it possible to locate the conductivity cell 55 or other acidity-measuring devices such as a direct titration cell in a separate shielded area remote from the sample vessel or pipe line.

The condenser temperature is controlled from the computer 63 through the temperature regulated cooling liquid supply 53 which controls the temperature of the cooling liquid passing through the condenser 51 to properly condense the acid vapor after which it flows into the conductivity measuring cell 55. The conductivity cell may be fabricated from pyrex tubing bent in a U-shape with two platinum electrodes 59 implanted in the inlet vertical leg of the cell vessel 55. The electrodes are typically 5-millimeter long sections of 2 millimeters i.d. bright, platinum tubing separated by 3 centimeters of flow cell length. Electrical connection to the platinum electrodes may be made by welding a 0.5-millimeter diameter platinum wire to the platinum tubing before sealing it in place in the tube 57 to contact the condensate flowing through the cell. The enlarged receiver end of the cell may be a 10-millimeter i.d. section of pyrex tubing reduced at one end and sealed to the inlet leg of the conductivity cell tube 57 to form a funnel to admit condensate and permit the escape of the sweep gas. The length of the vertical, cell-exit-tube 57 is adjusted so that a liquid level is maintained in the inlet funnel portion of the cell 55 just sufficient to prevent air bubbles from being drawn into the tube 57. Various conductivity meters 61 may be used to measure the condensate conductivity. One example of a conductivity-measuring device which may be used is a Radiometer-Copenhagen model CDM-2 supplied by The London Company, Cleveland, Ohio 44145. The output of the meter 61 is an analog signal which may be converted to a digital signal by means of the microcomputer 63 and the molarity of free acid in the sample is continuously calculated by plugging the conductivity measurement value into a special algorithm for calculating the sample molarity of free acid. The calculated molarity may be displayed in various forms such as on a strip chart recorder or a digital readout 71 as shown in FIG. 2B. In addition to controlling the system temperature and flow parameters as discussed above, the computer 63 is programmed to continually calculate and update the free acid molarity of the sample in accordance with the following algorithm:

$$[H^+] = (0.2 + 0.0175 - 2.1 \times 10^{-5} S^2 - 1.01 \times 10^{-8} S^3) K_T$$

wherein
  [H+] is the excess acid of the sample in Moles,
  S is the conductivity of the condensate in micro mhos, and
  $K_T$ is a temperature correction factor to normalize variation of evaporator temperature to 73° C. and is equal to $$K_I = 1.4 - 0.00027 T(100 - T)$$

wherein T is the temperature of the sample in °C. between 66° C. and 88° C.

It will be seen that the algorithm also requires the temperature at which the sample is evaporated and this is obtained from the temperature transducer 67 which measures the temperature of the sample leaving the evaporator vessel 27. In the specific embodiment shown in FIG. 2 the condenser temperature is maintained at about 21° C. at the cooling liquid (H$_2$O) inlet of the condenser 51. This produces a condensate flow rate of 10 milliliters per hour when the remainder of the operating conditions are as specified in the above disclosure.

Figure 4:
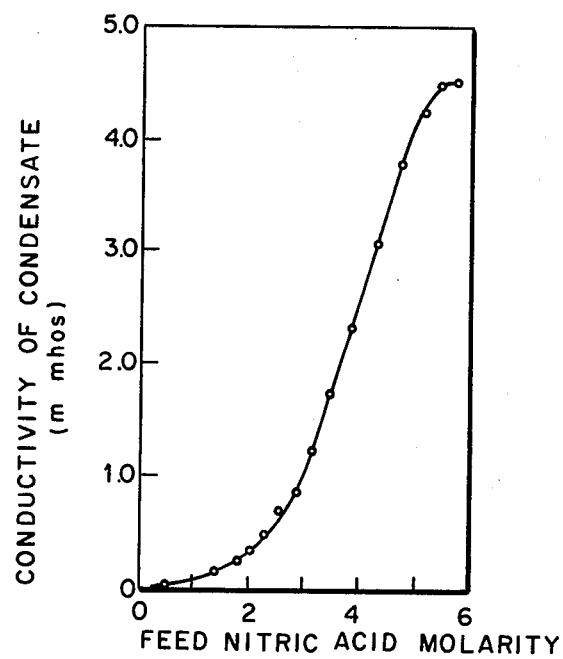
FIG. 4 is a typical conductivity response curve of the free acid monitor shown in FIG. 2 for feed nitric acid solutions of varying molarity.
Figure 5:
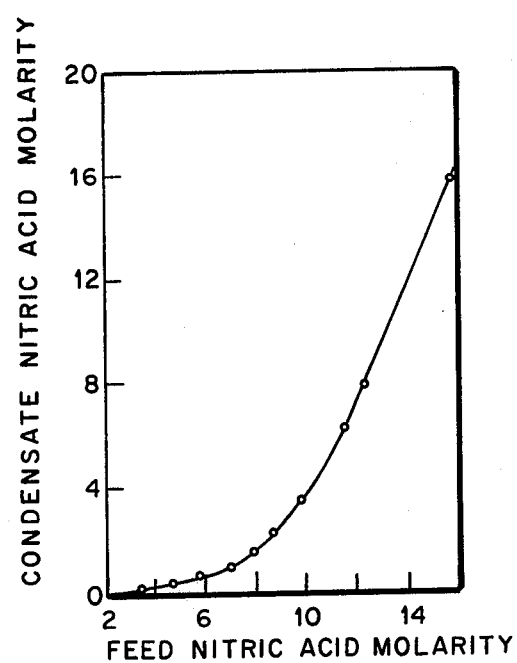
FIG. 5 is a typical response curve of the monitor using a direct titration measurement of the condensate.
Figure 6:
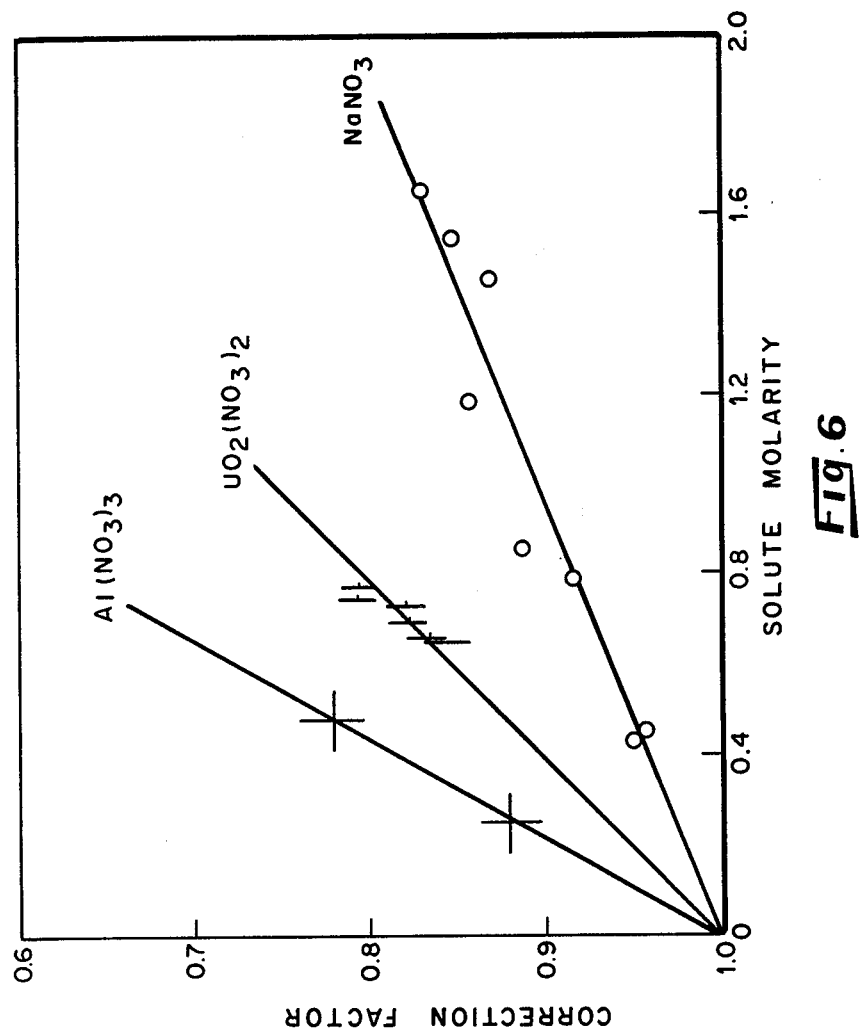
FIG. 6 is a plot of the effect of salute concentration on indicated free acid.

A typical response curve of the acid monitor is shown in FIG. 4. In this case, the system was filled with nitric acid and the effluent was monitored by means of a conductivity cell as shown in FIG. 2. The decrease in slope of the curve at a feed acid concentration of 10 molar is due to the decreasing conductivity of the condensate. This decrease in conductivity is caused by the decreased ionization of HNO$_3$ in strong acid solutions. For the particular system operating parameters as given above and using the algorithm provided above for the nitric acid monitoring system, the maximum conductivity of a nitric acid solution is observed in a 5.8 molar condensate solution. This corresponds to a sample nitric acid molarity of 10.8 M, which would be provided at the digital readout 71. When a direct titration of the condensate was used to monitor the condensate acidity the response was as shown in FIG. 5. The use of direct titration of the condensate extends the upper range of the monitor to above 14 molar but reduces the sensitivity at low acid levels and increases the response time because a larger volume of condensate is required. Thus, it will be appreciated that various means of measuring the condensate acidity and subsequently relating this measurement to the feed acidity may be used in carrying out the method of this invention.

With the conductivity measuring system as shown in FIG. 2, the response time of the monitor, that is the time necessary to correctly indicate the new acidity level after an alteration of the feed solution, is about 8 minutes at a condensate flow rate of 10 milliliters per hour. This response time is with the operating parameters as specified above which have been found to produce stable operation of the system shown in FIG. 2.

The presence of dissolved solids in the acid solution causes a positive bias in the monitor response. This bias is due to a common ion effect acting to suppress the ionization of nitric acid and thus increase the pHNO$_3$. FIG. 5 illustrates the correction that must be applied to convert the apparent excess acid to the true excess acidity for 3 different solutes. The curves were generated by adding solute or concentrated (15.7 M) nitric acid to the circulating acid. After equilibrium was obtained the excess acid was determined either by direct titration (when NaNO$_3$ was a solute) or complexometric titration (when Al(NO$_3$)$_3$ and UO$_2$(NO$_3$)$_2$ were the solutes). The solute concentration was determined gravimetrically. The excess acid ranged from 2 molar to 7 molar. The true excess acid was then divided by the indicated excess acid to obtain the correction factor. The estimated uncertainties in the data are indicated by the size of the individual data points.

From the figure, assuming that the major solute in the system herein disclosed is $UO_2(NO_3)_2$ at about 0.6 molar, it is only necessary to estimate the concentration of uranium within ±50% from feed information and apply a correction factor that will produce a monitor result that is within 5% of the true excess acid value.

Insoluble precipitates or residues that do not alter the partial pressure of either water or $HNO_3$ have no effect on the monitor response.

When the method is employed on a process line or vessel where there are no oxides of nitrogen present, the airlift type pump and subsequent separation chamber 13 may be eliminated and the sample circulation may be controlled by various other pumping means. Sample flow may be verified by monitoring the temperature at the outlet of the evaporator vessel 27 as shown in FIG. 2.

Thus it will be seen that a method has been provided whereby the free acid of an acid solution may be determined from the ratio of partial pressures of water and acid measured above the acid solution at constant temperature. The relative amounts of acid and water may be determined directly by measuring the acidity of the condensate formed by condensing the equilibrium vapor phase that exists above the acid solution by holding the temperature constant. The result of the condensate acidity measurement is related to the acidity of the original solution.

Further, it will be seen that apparatus has also been provided for carrying out the method of this invention wherein the acid solution is vaporized at a constant temperature, the generated vapors transported in vapor phase to a condenser and the condensate from the condenser is measured to determine its acid molarity which is directly related to the acidity of the acid solution. The apparatus may be embodied in a remotely controlled system for continuous-flow measurement of the acidity of a process stream and computer controlled to accomplish automatic readout of the acidity.

The foregoing description of a preferred embodiment of the invention has been presented for the purpose of illustration and description. It is not intended to be exhaustive or to limit the invention to the precise form disclosed; and obviously, many modifications and variations are possible in light of the above teachings. For example, a sensitive gas phase detector may be employed to simultaneously monitor the water vapor and acid vapor following the vaporization of the sample and thus more rapidly determine the free acid from relatively small samples. This would further reduce the response time to a change in the acidity level of the sample solution. The embodiment was chosen and described in order to best explain the principles of the invention in its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for measuring the free acid in an aqueous-acid solution, comprising the steps of:
   vaporizing a portion of said acid solution at a constant temperature to generate an equilibrium vapor phase of said solution; and
   determining the relative amounts of water and acid of said equilibrium vapor phase, said relative amounts being a measure of the free acid concentration of said solution.

2. The method as set forth in claim 1 wherein said determining step further includes condensing said equilibrium vapor and subsequently measuring the ratio of acid to water of the equilibrium vapor condensate.

3. The method as set forth in claim 2 wherein said aqueous-acid solution is contained in a process stream and further includes the step of diverting a portion of said process stream through a temperature-controlled flow-through vaporizer during said vaporizing step.

4. The method as set forth in claim 3 wherein said measuring step includes the steps of condensing said equilibrium vapor phase and measuring the conductivity of said condensate to determine the acidity of said equilibrium vapor and subsequently determining the free acid of said aqueous-acid solution relative to the acidity of said vapor phase.

5. The method as set forth in claim 4 wherein said acid solution is a nitric acid solution and wherein said step of determining the free acid of said solution includes calculating the free-acid of said aqueous-acid solution from said conductivity measurement in accordance with the following relationship:

$$[H^+] = (0.2 + 0.0175 - 2.1 \times 10^{-5}S^2 + 1.01 \times 10^{-8} S^3)K_T$$

wherein
$[H^+]$ is the moles of the excess acid of said solution,
S is the conductivity of the condensate in micro mhos, and
$K_T = 1.4 - 0.0002T(100-T)$
wherein
T is the temperature of said solution in a range of between 66° C. and 88° C.

6. A system for continuous-flow monitoring of the free acid of an acid solution comprising:
   a vaporizer;
   means for diverting a portion of said solution through said vaporizer;
   temperature control means for maintaining the temperature of said solution passing through said vaporizer at a predetermined constant temperature level sufficient to generate an equilibrium vapor phase of a portion of said solution passing through said vaporizer;
   a condenser means for condensing said equilibrium vapor phase;
   means for transporting said vapor phase from said vaporizer to said condenser;
   means for collecting the equilibrium vapor condensate from said condenser, and determining the relative amounts of the components of said collected condensate as a measure of the free acid of said acid solution.

7. The free-acid monitoring system as set forth in claim 6 wherein said transporting means includes a dry air supply means for passing a stream of dry air through said evaporator countercurrent to the flow of said solution to carry said vapor phase from said evaporator and a temperature-control means for maintaining said vapor phase transported thereby at a selected temperature level sufficient to prevent condensation of said vapor phase.

8. The free-acid monitoring system as set forth in claim 7 wherein said vaporizer and said temperature control means includes
- an outer casing, a vertically oriented evaporator vessel disposed within said outer casing and adapted to receive said solution at the top thereof, said evaporator vessel containing a plurality of partially interleaved baffles over which said solution flowing through said evaporator cascades, an excess solution exit line at the bottom thereof and a vapor exit line at the top thereof, and
- a temperature regulated evaporator heating liquid supply connected in fluid communication with the interior of said outer casing for circulating a heating liquid about said evaporator vessel to maintain said predetermined constant temperature level of said solution flowing through said vessel.

9. The free-acid monitoring system as set forth in claim 8 wherein said means for collecting said equilibrium vapor condensate and determining said relative amounts of the components of said condensate includes a conductive measuring cell for measuring the conductivity of said condensate as a relative measure of said free acid of said solution.

10. The free acid monitoring system as set forth in claim 9 wherein said monitoring system is a remote-controlled in-line system and wherein said diverting means includes means for pumping said portion of said process stream through said vaporizer and further including heat transfer means for returning the excess acid solution to said process stream at a predetermined temperature compatible with the temperature of said process stream, and a computer control means adapted to control said pumping means to provide a predetermined flow rate of acid solution through said vaporizer, monitoring the temperature of said solution passing through said vaporizer and controlling said evaporator heating liquid supply to maintain said predetermined temperature of said solution passing through said vaporizer, controlling said dry air supply flow rate and said transporting means temperature control means for a selected transport temperature and programmed to continuously calculate the free-acid of said process stream in response to said conductivity measurement values from said conductivity measuring cell.

* * * * *